United States Patent [19]

Berlin

[11] Patent Number: 5,169,312
[45] Date of Patent: Dec. 8, 1992

[54] DENTAL APPARATUS INTENDED FOR DRIVING AN INSTRUMENT FOR ENDODONTIC SURGERY

[75] Inventor: Pierre Berlin, La Chaux-De-Fonds, Switzerland

[73] Assignee: Instruments Dentaires S.A., La Chaux-De-Fonds, Switzerland

[21] Appl. No.: 865,202

[22] Filed: Apr. 8, 1992

[30] Foreign Application Priority Data

May 31, 1991 [CH] Switzerland .......................... 1617/91

[51] Int. Cl.⁵ .......................... A61C 1/07; A61C 3/03; A61C 3/08
[52] U.S. Cl. .................................... 433/123; 433/122; 433/112
[58] Field of Search ............... 433/102, 112, 118, 122, 433/123, 133

[56] References Cited

U.S. PATENT DOCUMENTS

| | | | |
|---|---|---|---|
| 987,732 | 3/1911 | Lyon | 433/112 X |
| 2,451,192 | 10/1948 | Blair | 433/133 |
| 3,578,745 | 5/1971 | Garnier | 433/122 X |
| 4,185,474 | 1/1980 | Kulischenko | 433/112 X |
| 4,341,519 | 7/1982 | Kuhn et al. | 433/122 |
| 4,629,426 | 12/1986 | Levy | 433/118 |
| 4,773,855 | 9/1988 | Levy | 433/102 |
| 4,781,588 | 11/1988 | Granier | 433/123 |
| 4,911,639 | 3/1990 | Jacklich | 433/102 |

FOREIGN PATENT DOCUMENTS 650678 9/1937 Fed. Rep. of Germany ...... 433/122
2645430 10/1990 France .

Primary Examiner—John J. Wilson
Assistant Examiner—Nicholas D. Lucchesi
Attorney, Agent, or Firm—Darby & Darby

[57] ABSTRACT

The apparatus of the contra-angle type comprises an instrument holder sleeve driven in a combined movement of alternate rotation and translation by an eccentric stud fixed to the end of a flexible shaft consisting of a metal cable. It comprises a device for controlling the flexibility of the end of the cable, this device consisting of a ring mounted rotatably in a support which can slide in the body of the apparatus.

4 Claims, 1 Drawing Sheet

DENTAL APPARATUS INTENDED FOR DRIVING AN INSTRUMENT FOR ENDODONTIC SURGERY

FIELD OF THE INVENTION

The invention relates to a dental apparatus intended for driving an instrument for endodontic surgery, comprising a body equipped with a head in which is freely mounted a sleeve intended to receive the instrument and driven in a combined movement of alternate rotation and translation by an eccentric stud fixed to the end of a flexible shaft driven in rotation by a drive means.

PRIOR ART

An apparatus of this type is known from the document FR-A-2,645,430. In this apparatus, the flexibility of the eccentric is obtained by the thinning of the first shaft which is generally found in a contra-angle between the head and the bend thereof. The flexibility thus obtained is supposed to make it possible to cancel the eccentric effect, that is to say the movement of the sleeve when the instrument is subjected to a high stress capable of causing it to break. However, the force necessary to bend the flexible shaft is unfortunately too great given the fragility of the instrument on which the high stress acts, with the result that there is every change that the instrument will break before succeeding in bending the shaft bearing the eccentric. In addition, it is not possible to reduce the diameter of this shaft below a certain limit, since the shaft would then become too fragile.

Furthermore, the boring of the dental canals is always a delicate operation, and it is carried out in a progressive manner using a range of endodontic instruments, fragile ones for small diameters, and then stronger and stronger ones as these diameters increase.

SUMMARY OF THE INVENTION

The present invention aims to produce a dental apparatus whose shaft driving the sleeve provides a real flexibility adapted to the resistance of the instrument and adaptable to the different resistances of instruments of different diameters.

The apparatus according to the invention is characterized in that the flexible shaft is a metal cable, and in that it comprises a means for controlling the flexibility of the end of the cable bearing the eccentric stud driving the sleeve.

The metal cable has the advantage of affording great flexibility allied with a high resistance, given that it consists of a multiplicity of very fine and strong steel wires. It is thus entirely possible to guarantee a flexibility adapted to the finest instruments.

By using a cable in combination with a means for controlling the flexibility of the end of the cable, it is possible to adapt the flexibility to the resistance of the instrument mounted in the head of the apparatus.

A simple control means consists of a ring which is mounted rotatably in the body of the apparatus and through which the cable passes, this ring being displaceable along the cable.

The use of a cable additionally makes it possible to omit the gears present in the conventional contra-angles and, consequently, to simplify the design of the apparatuses.

The use of a cable would even make it possible to have an articulated bend.

BRIEF DESCRIPTION OF THE DRAWINGS

The attached drawing shows, by way of example, an embodiment of the invention.

The single FIGURE in the drawing is a longitudinal cutaway view of a contra-angle.

DESCRIPTION OF THE PREFERRED EMBODIMENT

Figure 1:
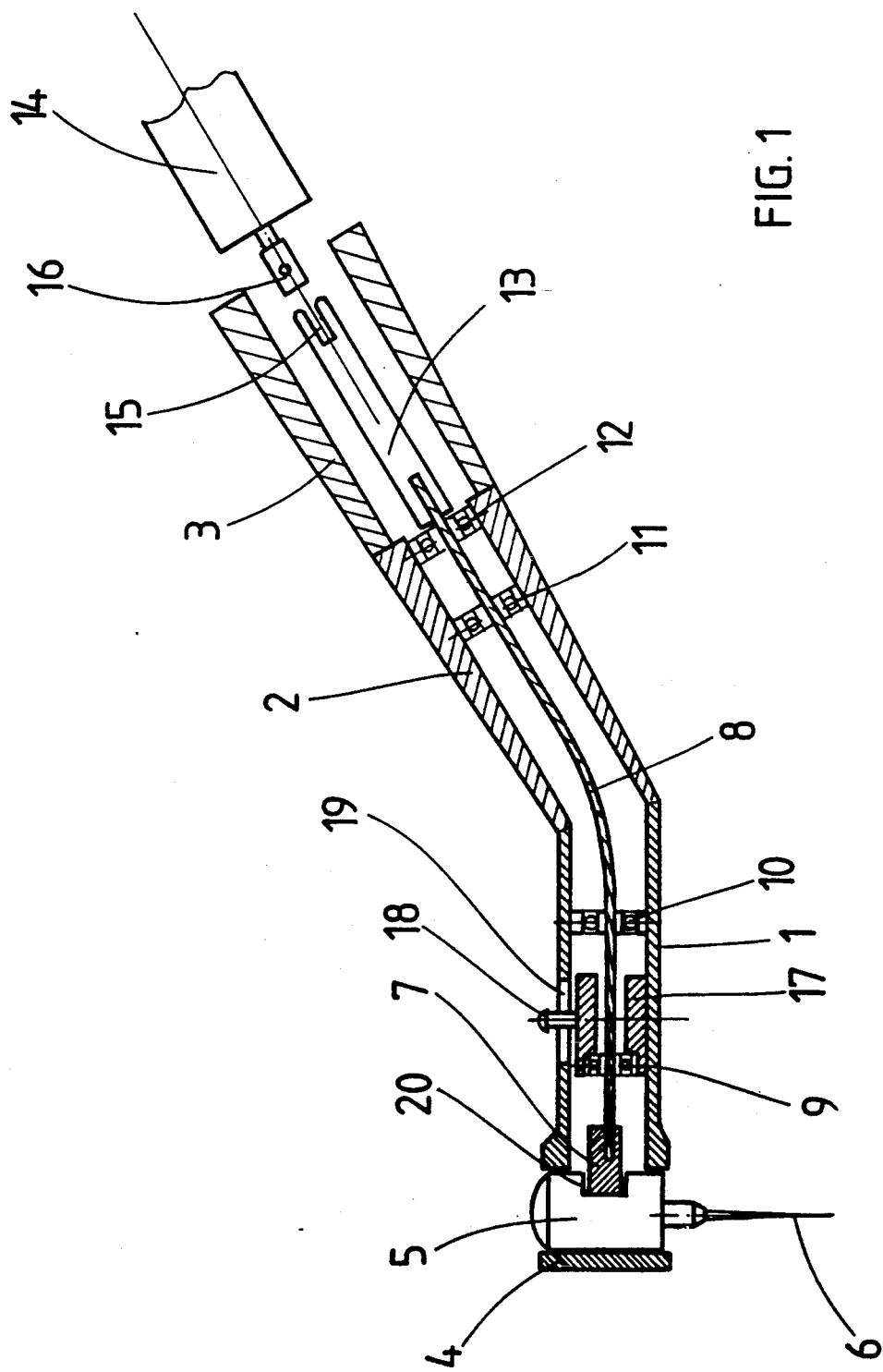

The contra-angle shown comprises a bent body consisting in a known manner of three parts 1, 2 and 3, the part 1 ending in a head 4 having a cylindrical bore in which is mounted a sleeve 5 equipped with a clamp in which an instrument or tool 6 is fixed. The sleeve 5 is conventional. It is equipped with a radial cylindrical seat 20 in which is engaged a cylindrical stud 7 fixed eccentrically to the end of a steel cable 8. The cable 8 is held by the inner raceways of four ballbearings 9, 10, 11 and 12 and its other end is fixed to a standardized drive component 13 which can be coupled to a motor 14 by conventional coupling means 15 and 16.

The outer rings of the ballbearings 10, 11 and 12 are fixed to the body, for example by nailing, and the inner raceways of these ballbearings are mounted on the cable 8 with a sufficient friction to ensure that they are driven in rotation by the cable.

The ballbearing 9 is mounted in a support 17 mounted slidably in the front part 1 of the body of the contra-angle and is equipped with a radial pin 18 passing through the body via a longitudinal slot 19 in such a way as to allow the sliding support 17 to be displaced by the user. The internal diameter of the inner raceway of the ballbearing 9 is such that the ballbearing can be easily displaced by hand along the cable 8. The length of the slot 19 is such that the ballbearing 9 can be brought very close to the eccentric stud 7.

The flexibility of the mounting of the eccentric stud 7 depends on the length of cable between this stud and the ballbearing 9. By displacing the sliding support 17, it is thus possible to vary the flexibility of this mounting between a value of practically zero and a very high value corresponding to a position in which the sliding support 17 is practically in abutment against the ballbearing 10.

The user can thus modify the flexibility of the drive stud as a function of the instrument used. It is possible, for example, to envisage three positions, namely a position of maximum flexibility for very fine instruments, an intermediate position making it possible to work with instruments of medium dimensions as far as the apical zone, and a position of practically zero flexibility for larger instruments, in particular for the rapid widening of the coronal third of the canal.

The cable can be driven by any drive means available.

I claim:

1. A dental apparatus intended for driving an instrument for endodontic surgery, comprising a body (1, 2, 3) equipped with a head (4) in which is freely mounted a sleeve (5) intended to receive the instrument (6) and which is driven in a combined movement of alternate rotation and translation by an eccentric stud (7) fixed to the end of a flexible shaft driven in rotation by a drive means, wherein the flexible shaft is a metal cable (8) and wherein the apparatus comprises a means (9, 17) for controlling the flexibility of the end of the cable bearing the eccentric stud.

2. The dental apparatus as claimed in claim 1, wherein the means for controlling the flexibility of the end of the cable consists of a ring (9) which is mounted rotatably in the body and through which the cable passes, said ring being displaceable in the body along the cable.

3. The dental apparatus as claimed in claim 2, wherein said ring (9) is mounted rotatably in a support (17) mounted slidably in the body of the apparatus.

4. The dental apparatus as claimed in claim 3, wherein said ring (9) consists of the inner raceway of a ballbearing.

* * * * *